(12) United States Patent
Budhiraja et al.

(10) Patent No.: US 11,992,610 B2
(45) Date of Patent: May 28, 2024

(54) EXTERNAL SENSOR ARRANGEMENT FOR PATIENT INTERFACE

(71) Applicant: Fisher & Paykel Healthcare Limited, Auckland (NZ)

(72) Inventors: Nimansha Budhiraja, Auckland (NZ); Nordyn Alami, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 454 days.

(21) Appl. No.: 17/459,333

(22) Filed: Aug. 27, 2021

(65) Prior Publication Data

US 2021/0393900 A1    Dec. 23, 2021

Related U.S. Application Data

(63) Continuation of application No. 16/161,950, filed on Oct. 16, 2018, now Pat. No. 11,135,381, which is a
(Continued)

(51) Int. Cl.
*A61M 16/00* (2006.01)
*A61M 16/06* (2006.01)
*A61M 16/16* (2006.01)

(52) U.S. Cl.
CPC .... *A61M 16/0003* (2014.02); *A61M 16/0605* (2014.02); *A61M 16/0616* (2014.02); *A61M 16/0633* (2014.02); *A61M 16/16* (2013.01); *A61M 2016/0027* (2013.01); *A61M 2016/0033* (2013.01); *A61M 16/161* (2014.02);
(Continued)

(58) Field of Classification Search
CPC .............. A61M 16/0003; A61M 16/06; A61M 16/0616; A61M 16/0622; A61M 16/0633; A61M 2016/0027; A61M 2016/0033; A61B 5/087; A61B 5/0878
See application file for complete search history.

(56) References Cited

U.S. PATENT DOCUMENTS

| 3,910,261 A | 10/1975 | Ragsdale et al. |
| 5,063,938 A | 11/1991 | Beck et al. |
| (Continued) |

FOREIGN PATENT DOCUMENTS

| AU | 2008 202 677 A1 | 1/2010 |
| EP | 2319569 A2 | 5/2011 |
| (Continued) |

OTHER PUBLICATIONS

EPO Search Report 13837854.2; dated Mar. 17, 2016; 6 pages.
(Continued)

*Primary Examiner* — Joseph D. Boecker
(74) *Attorney, Agent, or Firm* — Knobbe, Martens, Olson & Bear LLP

(57) ABSTRACT

A patient interface mask for use with a breathing assistance apparatus includes a seal that, in use, circumscribes a nose, mouth, or nose and mouth of a patient and defines an interior space of the mask. The mask includes an inlet into the interior space and an outlet from the interior space. A sensor is positioned outside of the interior space and in the path of exit gases exiting the interior space through the outlet. The sensor detects a parameter of the exit gases, such as temperature, humidity or both.

20 Claims, 3 Drawing Sheets

Related U.S. Application Data continuation of application No. 14/428,305, filed as application No. PCT/IB2013/058389 on Sep. 9, 2013, now Pat. No. 10,124,134.

(60) Provisional application No. 61/701,145, filed on Sep. 14, 2012.

(52) U.S. Cl.
CPC . *A61M 2205/33* (2013.01); *A61M 2205/3327* (2013.01); *A61M 2205/3334* (2013.01); *A61M 2205/3344* (2013.01); *A61M 2205/3368* (2013.01)

(56) References Cited

U.S. PATENT DOCUMENTS

| | | | |
|---|---|---|---|
| 5,857,460 | A | 1/1999 | Popitz |
| 6,017,315 | A | 1/2000 | Starr et al. |
| 6,273,087 | B1 | 8/2001 | Boussignac et al. |
| 6,277,645 | B1 | 8/2001 | Mault |
| 6,612,306 | B1 * | 9/2003 | Mault ............ A61B 5/6838 128/200.22 |
| 9,138,169 | B2 | 9/2015 | Beard |
| 10,124,134 | B2 | 11/2018 | Budhiraja et al. |
| 2002/0029004 | A1 | 3/2002 | Starr et al. |
| 2002/0122746 | A1 | 9/2002 | Yamamori et al. |
| 2004/0210151 | A1 * | 10/2004 | Tsukashima ........... A61B 5/083 600/532 |
| 2006/0249160 | A1 | 11/2006 | Scarberry et al. |
| 2008/0078391 | A1 | 4/2008 | Jensen |
| 2008/0092898 | A1 | 4/2008 | Schneider et al. |
| 2008/0196715 | A1 | 8/2008 | Yamamori |
| 2009/0107501 | A1 | 4/2009 | Krieger |
| 2009/0223521 | A1 | 9/2009 | Howard et al. |
| 2009/0293881 | A1 | 12/2009 | Graham |
| 2010/0108070 | A1 | 5/2010 | Kwok |
| 2010/0170513 | A1 | 7/2010 | Bowditch |
| 2010/0275919 | A1 | 11/2010 | Sung |
| 2011/0015534 | A1 | 1/2011 | Yamamori |
| 2011/0030692 | A1 | 2/2011 | Jones |
| 2011/0094513 | A1 | 4/2011 | Takatori et al. |
| 2012/0318266 | A1 | 12/2012 | Chou |
| 2013/0060157 | A1 | 3/2013 | Beard |

FOREIGN PATENT DOCUMENTS

| | | |
|---|---|---|
| EP | 2895225 B1 | 8/2017 |
| WO | WO 97/033641 | 9/1997 |
| WO | WO 97/033651 | 9/1997 |
| WO | WO 01/43804 A1 | 6/2001 |
| WO | WO 2012/037641 A1 | 3/2012 |

OTHER PUBLICATIONS

European Extended Search Report, EP 17 19 8569 dated Feb. 5, 2018.
European Patent Office intention to grant dated Feb. 5, 2017.
Examination Report received in European Application No. 17198569, dated Feb. 25, 2019.
International Search Report; PCT/IB2013/058389; dated Jan. 22, 2014; 5 pages.
Response to examination report as filed dated Sep. 30, 2016.
Written Opinion; PCT/IB2013/058389; dated Jan. 22, 2014; 5 pages.

* cited by examiner

EXTERNAL SENSOR ARRANGEMENT FOR PATIENT INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to a breathing apparatus including but not solely limited to a breathing apparatus providing pressure therapy (such as PAP machines or similar) for treating obstructive sleep apnea and/or breathing apparatus providing flow and/or humidification therapy for treating chronic or respiratory disorders.

Description of the Related Art

Breathing apparatus exist that provide flow and/or pressure therapy to a patient. The flow and/or pressure can be delivered to the patient via an interface, such as a mask. The mask can be a nasal mask, an oral mask or a full face mask. It can be helpful to measure properties of the gas within the mask, such as humidity or temperature of the gas, for example.

SUMMARY OF THE INVENTION

However, positioning the sensor within the mask (or elsewhere within the patient breathing circuit) can be disadvantageous due to toxicology or biocompatibility issues. These issues can be addressed, but often at an added cost. Therefore, preferred patient interfaces disclosed herein position the sensor external of the mask (or other patient interface) and patient breathing circuit. An added advantage of such an arrangement is that the sensor is not constantly exposed to the high humidity environment of the interior of the mask, which increases the reliability and/or lifespan of the sensor.

A preferred embodiment involves a patient interface mask for use with a breathing assistance apparatus includes a seal that, in use, circumscribes a nose, mouth, or nose and mouth of a patient and defines an interior space of the mask. The mask includes an inlet into the interior space and an outlet from the interior space. A sensor is positioned outside of the interior space and in the path of exit gases exiting the interior space through the outlet. The sensor detects a parameter of the exit gases.

In some arrangements, the sensor is positioned forward of the outlet.

In some arrangements, the mask includes a body that defines the outlet, and the sensor is spaced from the body forward of the outlet.

In some arrangements, the sensor is removable from the mask.

In some arrangements, the sensor is supported relative to the mask by a support arrangement. The support arrangement can surround the inlet. The support arrangement can be removable from the mask. In some cases, the support arrangement comprises two halves. The halves can be split along a vertical plane.

In some arrangements, the sensor detects temperature, humidity or both.

In some arrangements, the sensor includes an integrated memory, power source or both.

In some arrangements, the sensor is coupled for electronic communication with a component of the breathing assistance apparatus. The component can be a flow generator or a humidifier and the electronic communication between the sensor and the component enables feedback control of the component.

BRIEF DESCRIPTION OF THE DRAWINGS

Preferred embodiments are described with reference to the following drawings, which are intended to illustrate and not to limit the disclosure.

DETAILED DESCRIPTION OF THE PREFERRED EMBODIMENTS

In the present specification, breathing apparatus (which can also be referred to as a respiratory assistance apparatus/ system) can mean among other things an apparatus for providing flow therapy or an apparatus for providing pressure therapy. Breathing apparatus for providing humidified and heated gases to a patient (either as flow or pressure therapy for example as CPAP for treating OSA or flow therapy for treating chronic respiratory disorders) for therapeutic purposes are well known in the art. Systems for providing therapy of this type (for example respiratory humidification) typically have a structure where gases are delivered to a humidifier chamber from a gases source, such as a blower (also known as a compressor, an assisted breathing unit, a fan unit, a flow generator or a pressure generator). A controller (processor) controls operation of the apparatus. As the gases (fluid) pass over the hot water, or through the heated and humidified air in the humidifier chamber, they become saturated with water vapor. The heated and humidified gases are then delivered to a user or patient downstream from the humidifier chamber, via a gases conduit and a user interface. A breathing apparatus to provide flow therapy controls the flow rate of gas (e.g., air and/or oxygen) to the patient. A breathing apparatus to provide pressure therapy controls the pressure provided to the patient.

Figure 1:
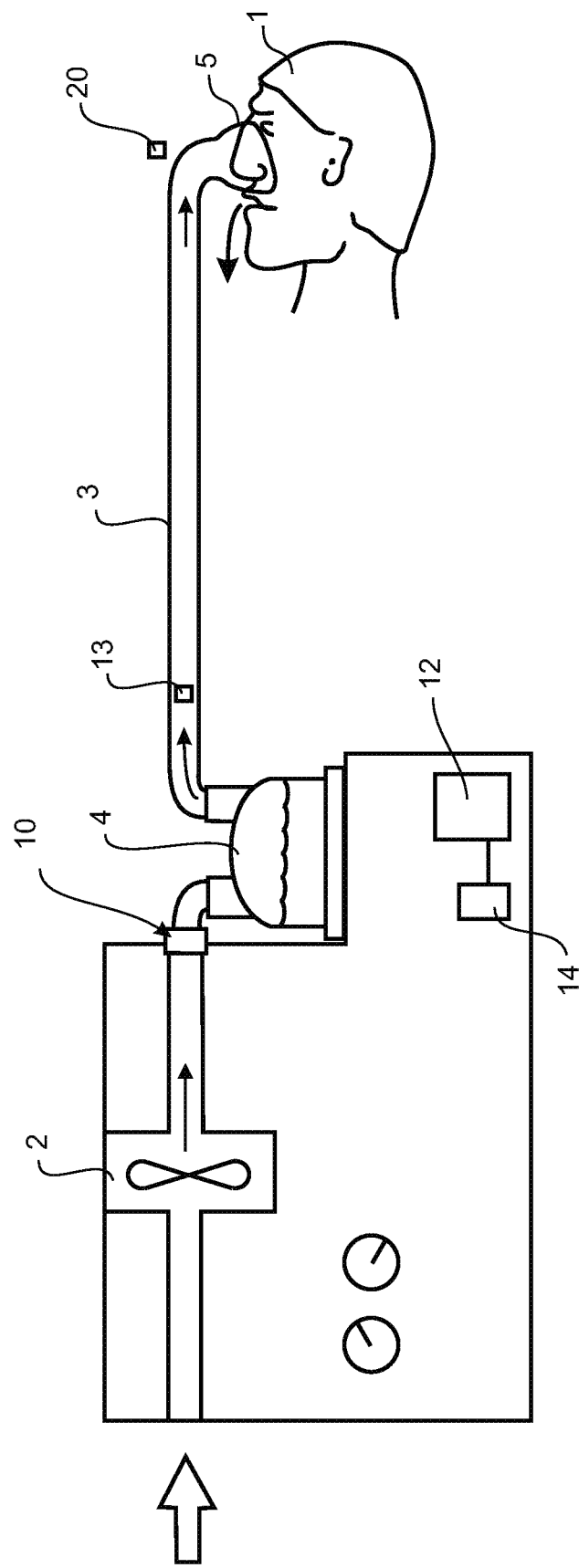
FIG. 1 illustrates a flow therapy breathing apparatus, such as a positive airway pressure (PAP) or continuous positive airway pressure (CPAP) apparatus, which incorporates a patient interface or mask having an external sensor.

FIG. 1 shows a breathing apparatus (e.g., a CPAP device) for providing flow therapy and/or humidification therapy for treating respiratory disorders. In one form, such breathing apparatus can be modular and comprise a humidifier unit and a blower unit that are separate (modular) items. The modules are connected in series via connection conduits to allow gases to pass from the blower unit to the humidifier unit. In another embodiment, the blower unit and humidifier unit are integrated ("integrated unit"). In either case, a flow of air (and optionally oxygen) (more generally "fluid or gas flow") is provided by a blower unit through a humidification chamber and then through a conduit and patient interface so that the humidified flow is provided to a patient.

With reference to FIG. 1, a user 1 receives a stream of heated and humidified air/oxygen (fluid or gas) from a breathing apparatus 10. Gas flow is provided from blower unit 2 to a humidifier chamber 4, for example, via a connector conduit. The stream of humidified, heated and pressurized gas exits the humidification chamber 4 via a user conduit 3, and is provided to the patient or user 1 via a user interface 5. The process can be controlled by a controller 12. The apparatus preferably also has sensors, such as temperature, humidity, pressure and/or flow sensors 13 and/or 20, for detecting operating parameters of the apparatus or parameters of the breathing gas (supplied or expired). The controller 12 can control operations of the breathing apparatus, including fan speed and humidification level. The controller 12 can also receive feedback from sensors 13, 20 (and/or other sensors) to control operation of the breathing apparatus. The controller 12 can also record compliance or other operation or sensor data onto a memory 14. In some arrangements, as described herein, the sensors 13 and/or 20 can record information on a local or integrated memory.

The user interface 5 shown in FIG. 1 is a nasal mask by way of example. However, it should be noted that in systems of these types, a full face mask that covers the mouth and nose, an oral mask that covers only the mouth or any other suitable user interface could be substituted for the nasal mask shown.

A common mode of operation as controlled by the controller 12 is as follows: air is drawn by the blower 2 through an inlet into the casing which surrounds and encloses at least the blower portion 2 of the system. The blower 2 generates an air stream from the flow generator outlet and passes this into the humidifier chamber 4. The air stream is heated and humidified in the humidifier chamber, and exits the humidifier chamber via an outlet. A flexible hose or conduit 3 is connected either directly or indirectly to the humidifier outlet, and the heated, humidified gases are passed to a user 1 via the conduit 3.

The gases provided by the blower 2 can be sourced from the surrounding atmosphere. However, some forms of these systems may be configured to allow a supplementary gas (e.g. oxygen) to be blended with the atmospheric air for particular therapies. In such systems, a gases conduit supplying the supplemental gas is typically either connected directly to the humidifier chamber or elsewhere on the high pressure (flow outlet) side of the blower unit, or alternatively to the inlet side of the blower unit.

Figure 3:
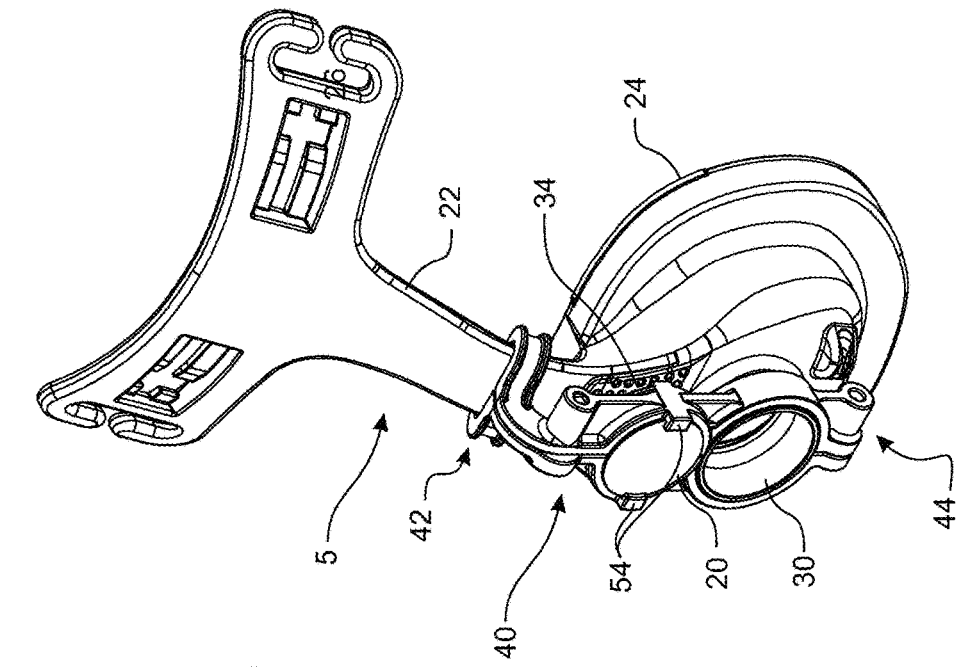
FIG. 3 is a perspective view of the nasal mask of FIG. 2 with the sensor and support arrangement assembled to the mask.
Figure 2:
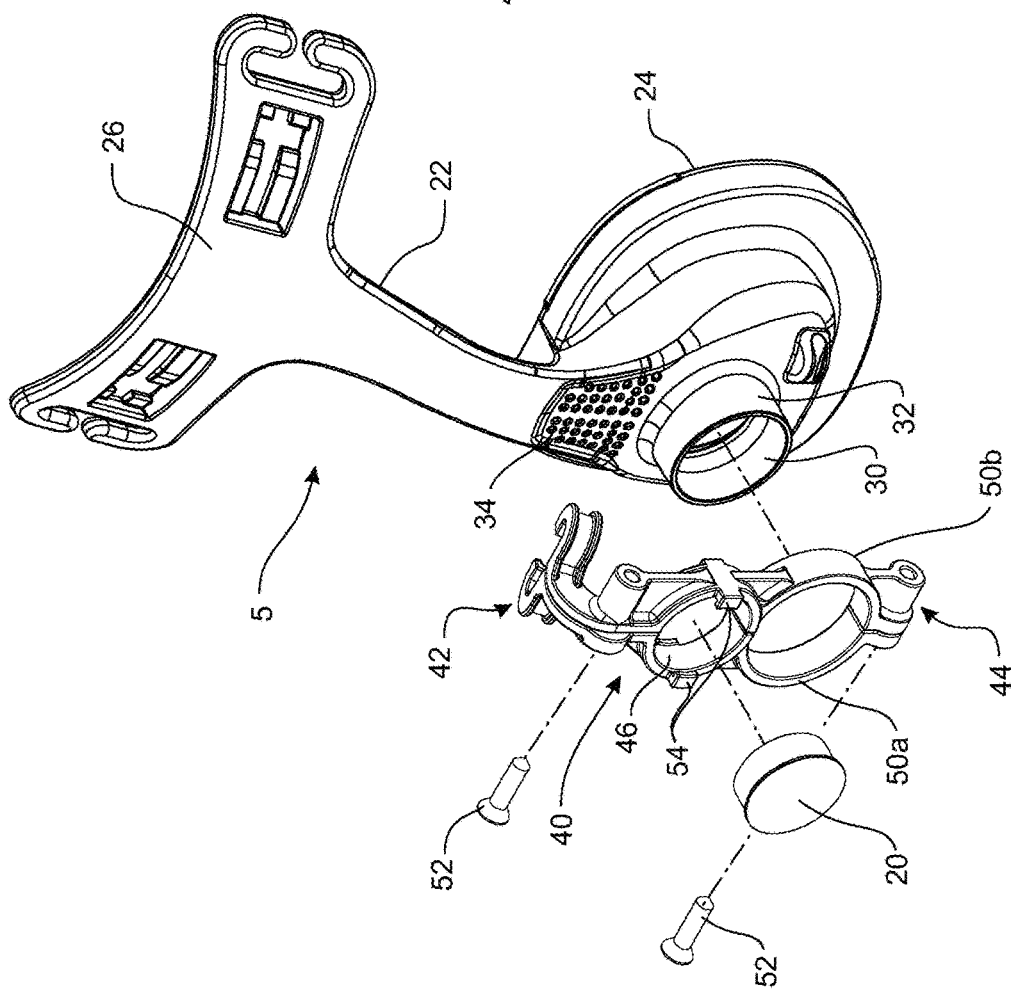
FIG. 2 is a perspective view of a nasal mask with the sensor and support arrangement separated from the mask.

FIGS. 2 and 3 illustrate an embodiment of a patient interface 5 with an external sensor 20. The illustrated patient interface 5 is a nasal mask, which includes a mask body comprising a frame 22 and a seal 24. The frame 22 can include a strap or headgear interface portion 26, which allows the frame 22 to be secured to a strap or headgear (not shown) that assists in retaining the nasal mask 5 on the user 1. The strap or headgear, or another strap, can engage another portion of the nasal mask 5 to assist in securing a bottom portion of the nasal mask 5 to the user 1. The nasal mask 5 can be, for example, any suitable one of the Zest™ line of nasal masks sold by Fisher & Paykel Healthcare.

The seal 24 is sized and shaped to circumscribe the nose or nares of the user 1 and create at least a substantial seal with the user's face. The nasal mask 5 includes an inlet 30 defined by a boss 32, which is generally or substantially cylindrical in shape in the illustrated arrangement. The inlet 30 opens to an interior of the nasal mask 5. The supply conduit 3 (FIG. 1) is coupled to the boss 32 and provides breathing gas from the breathing apparatus 10 (FIG. 1) to the interior of the mask 5 through the inlet 30.

The nasal mask 5 also includes an outlet, which in the illustrated arrangement is a bias flow outlet 34 comprised of a plurality of exit holes. The outlet 34 permits gases to exit from the interior of the mask 5 to an atmosphere external of the mask 5. The gases exiting the mask 5 can be unused breathing gas supplied to the mask 5 from the breathing apparatus 10, expired gases from the user 1 or a combination of both.

The sensor 20 is positioned near the outlet 34 and, preferably, directly forward of the outlet 34. Preferably, the sensor 20 is spaced from the outlet 34 a sufficient distance to avoid any significant obstruction of the gases exiting the outlet 34. The sensor 20 can be any type of sensor that detects a useful parameter of the breathing gases. In one arrangement, the sensor 20 is a temperature and/or humidity sensor. The sensor 20 could detect either or both of these parameters or other parameters (such as but not limited to flow and/or pressure) in addition or in the alternative. Preferably, the sensor 20 has a built-in memory to record the measured data and a battery (or other power source) to power the device. One suitable sensor 20 is the DS1923 hygrochron iButton® sold by Maxim Integrated.

The sensor 20 can be used to collect data for use in developing algorithms for use in the control system (e.g., controller 12) of the breathing apparatus 10. That is, the sensor 20 can be used to collect data that provides information regarding the relationship between the settings of the breathing apparatus 10 and the conditions within the interior of the mask 5. The data can also be correlated to feedback from the user 1 regarding the user's preferences about the humidity settings. This information can be used in product development (e.g., design or operational settings) of the breathing apparatus 10 or any component or accessory thereof (e.g., interface (mask), flow generator, humidifier, conduit).

In addition or in the alternative, the sensor 20 can communicate with the control system (e.g., controller) of the breathing apparatus 10, such as through wired or wireless communication. The sensor 20 can provide sensor data, which can be correlated to the conditions of the gases within the mask 5, to the breathing apparatus 10 for closed-loop or feedback control of the humidity and temperature functions (possibly among other functions). That is, the breathing apparatus 10 can control its internal parameters (e.g., heater plate or water temperature and power input to the heated breathing tube) to maintain desired humidity and temperature at the mask 5.

The information utilized by the system can include both detected data (e.g., temperature and humidity) and information that can be determined from, estimated from or correlated to the detected data (e.g., presence or absence of condensation within the mask interior or amount of condensation in the mask interior). Inside the mask is the mixture of gas properties of the air supplied by the breathing apparatus 10 (e.g., CPAP) and the expired air by the patient 1. During inhalation, the properties in the mask can be very close to the CPAP delivery air. During exhalation, the air is a mixture of the CPAP air and the patient expired air. It is of particular interest to determine the relative humidity and temperature inside the mask as these parameters directly relate to the condensation in the mask. Accordingly, this information can be used to change unit settings to limit or prevent condensation in the mask, through a feedback control system and/or by using the collected data to improve the operational algorithms, settings or other operational parameters of the breathing apparatus 10. The sensor data during either inhalation, exhalation, or both, can be utilized.

The sensor 20 can be supported by any suitable arrangement, which can permit the sensor 20 to be separable from the mask 5 or can integrate the sensor 20 with the mask 5. Thus, the sensor 20 can be removable from the mask 5 or permanently secured to the mask 5. In the illustrated arrangement, the sensor 20 is supported relative to the mask 5 by a support arrangement 40 that is separable from the mask 5. Preferably, the support arrangement 40 releasably engages the frame 22 of the mask 5. In particular, the support arrangement 40 has a first portion 42 that engages a first portion (e.g., a vertical strut portion) of the frame 22 and a second portion 44 that engages a second portion (e.g., the inlet boss 32) of the frame 22. The support arrangement 40 also includes a cavity 46 that receives and supports the sensor 20 and positions the sensor 20 in front of the outlet 34.

In some arrangements, the support arrangement 40 can include a plurality of portions connectable to one another. In the illustrated arrangement, the support arrangement 40 includes two halves 50a, 50b, which can be coupled by any suitable arrangement, such as one or more fasteners 52 (e.g., threaded fasteners or self-tapping threaded fasteners). The halves 50a, 50b can be split along a vertical plane, as illustrated, or in any other suitable direction. The support arrangement 40 can include tabs 54 (e.g., forward and rearward tabs 54) that extend at least partially across the cavity 46 to retain the sensor 20 within the cavity 46. Such an arrangement allows the support arrangement 40 (and sensor 20) to be conveniently assembled to the nasal mask 5, such as without removing the patient conduit 3 from the mask 5. Accordingly, the support arrangement 40 can be assembled to one nasal mask 5 to collect data for a period of time and then removed and assembled to another nasal mask 5.

Figure 5:
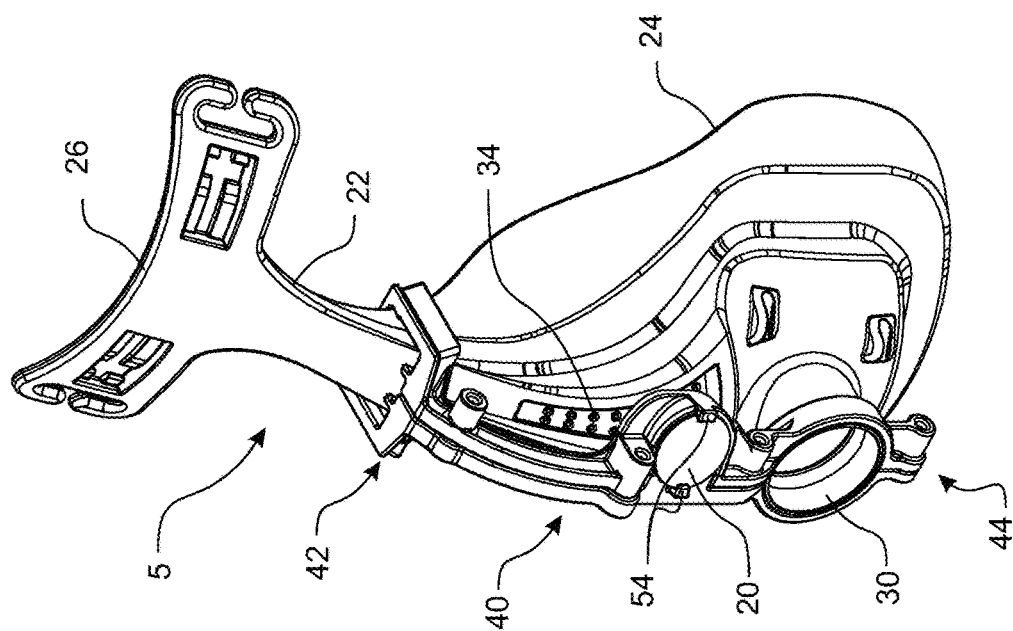
FIG. 5 is a perspective view of the full face mask of FIG. 4 with the sensor and support arrangement assembled to the mask.
Figure 4:
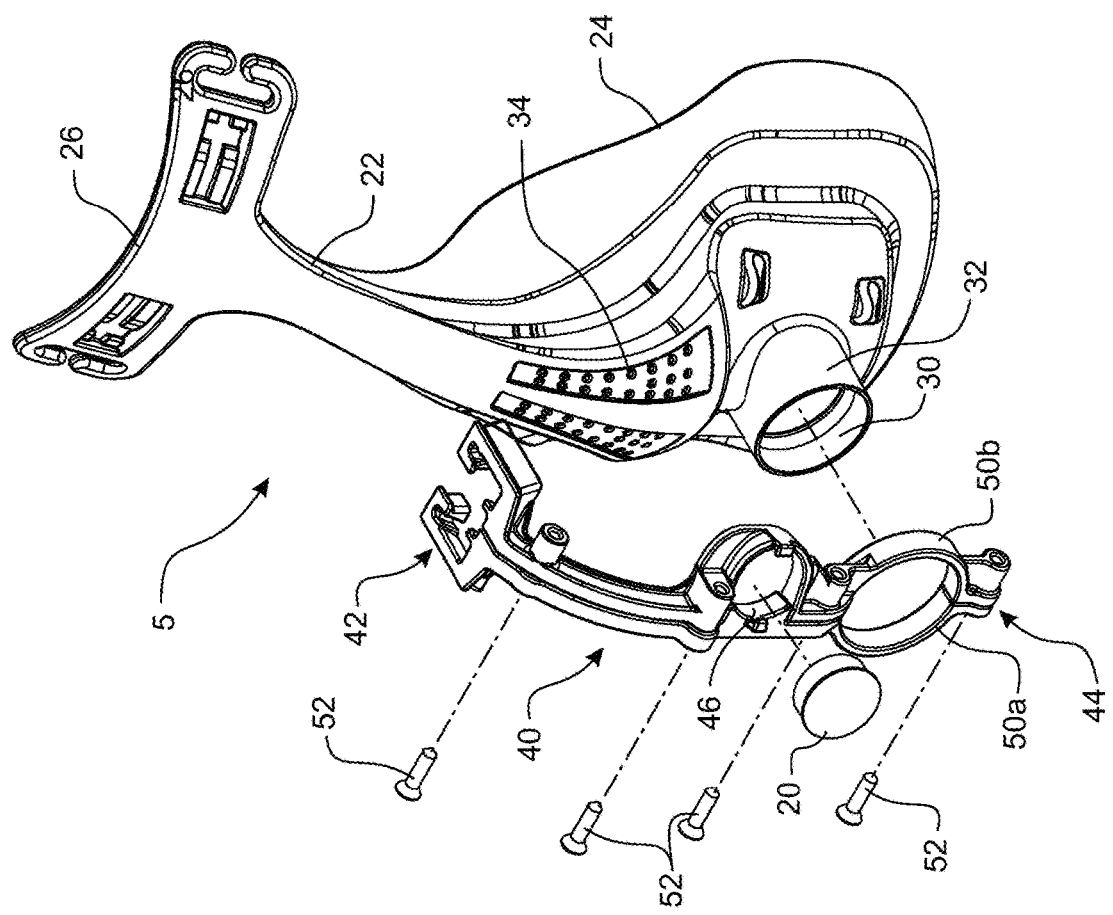
FIG. 4 is a perspective view of a full face mask with the sensor and support arrangement separated from the mask.

FIGS. 4 and 5 illustrate a full face mask 5 that includes a support arrangement 40, which supports a sensor 20 in a position forward of the outlet 34 of the mask 5. The full face mask 5 is sized and shaped to circumscribe both the nose and mouth of a user 1. Thus, the full face mask 5 has a vertical dimension or length that is greater than the vertical dimension or length of the nasal mask 5 of FIGS. 1-3. Accordingly, the support arrangement 40 of FIGS. 4 and 5 is longer than the support arrangement 40 of FIGS. 2 and 3. Additional fasteners 52 (e.g., four instead of two) may be used with the support arrangement 40 of FIGS. 4 and 5. In other respects, the mask 5, support arrangement 40, sensor 20 and operation of the system can be the same as or similar to previously-described mask 5, support arrangement 40, sensor 20 and system. The mask 5 can be, for example, any one of the Zest™ line of nasal masks sold by Fisher & Paykel Healthcare.

Advantageously, the sensor 20 being positioned outside of the patient breathing circuit doesn't present any toxicology risk/biocompatibility issue for the patient. In addition, the level of humidity inside the mask is often very high due to patient exhalation. By positioning the sensor 20 outside of the mask 5, the sensor 20 will not be constantly and entirely exposed to this high humidity, which is an added advantage.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

What is claimed is:

1. A patient interface mask for use with a breathing assistance apparatus, the patient interface mask comprising:
    a seal that, in use, circumscribes at least one of a nose and a mouth of a patient, the seal at least partially defining an interior space of the mask;
    an inlet into the interior space that is configured to receive breathing gases from the breathing assistance apparatus;
    an outlet from the interior space;
    a sensor that, in use, detects a parameter of exit gases exiting the interior space through the outlet, wherein the exit gases are at least one of unused breathing gases supplied to the mask from the breathing assistance apparatus and expired gases from the patient; and
    a support arrangement that positions the sensor in a path of the exit gases exiting through the outlet and spaced from the outlet by a distance, the space between the sensor and the outlet being open to atmosphere, the support arrangement comprising two portions that are removably connected to one another, the two portions defining a cavity when connected together, the cavity receiving the sensor;
    the sensor providing sensor data correlated to gases conditions within the mask.

2. The patient interface mask of claim 1, wherein the two portions are split along a vertical plane.

3. The patient interface mask of claim 1, further comprising a frame that couples with the seal, wherein the support arrangement can engage the frame.

4. The patient interface mask of claim 3, wherein the support arrangement can releasably engage the frame.

5. The patient interface mask of claim 3, wherein the support arrangement comprises a first end and a second end opposite the first end, and wherein the first end of the support arrangement can engage the frame.

6. The patient interface mask of claim 5, wherein the first end of the support arrangement can engage a vertical strut portion of the frame.

7. The patient interface mask of claim 6, wherein the first end of the support arrangement wraps around at least a portion of the frame.

8. The patient interface mask of claim 1, wherein the cavity comprises a circular shape.

9. The patient interface mask of claim 1, wherein the two portions are connected with one or more fasteners.

10. The patient interface mask of claim 1, further comprising at least one tab extending at least partially across the cavity, the at least one tab retaining the sensor within the cavity.

11. A system comprising the patient interface mask of claim 1 and the breathing assistance apparatus.

12. A patient interface mask for use with a breathing assistance apparatus, the patient interface mask comprising:
- a mask body that is secured to a face of a patient when in use, the mask body at least partially defining an interior space;
- the mask also comprising an inlet that is in fluid communication with the interior space and configured to receive breathing gases from the breathing assistance apparatus;
- the mask also comprising an outlet that is in fluid communication with the interior space;
- a sensor that, in use, detects a parameter of exit gases exiting the interior space through the outlet; and
- a support arrangement positioning the sensor in a path of the exit gases exiting from the interior space, wherein the support arrangement comprises two portions that are removably connected to one another, the two portions defining a cavity when connected together, the cavity receiving the sensor.

13. The patient interface mask of claim 12, wherein the support arrangement spaces the sensor away from the outlet by a distance.

14. The patient interface mask of claim 13, wherein the distance between the sensor and the outlet is open to atmosphere.

15. The patient interface mask of claim 12, wherein the sensor provides sensor data correlated to gases conditions within the mask.

16. The patient interface mask of claim 12, wherein the two portions are connected together with one or more fasteners.

17. The patient interface mask of claim 12, further comprising at least one tab extending at least partially across the cavity, the at least one tab retaining the sensor within the cavity.

18. The patient interface mask of claim 12, wherein the mask body comprises a frame and a seal coupled to the frame, the seal circumscribing at least one of a nose and a mouth of the patient when in use.

19. The patient interface mask of claim 18, wherein the support arrangement comprises a first end and a second end opposite the first end, and wherein the first end of the support arrangement engages the frame.

20. The patient interface mask of claim 19, wherein the first end of the support arrangement wraps around at least a portion of the frame.

* * * * *